United States Patent [19]

Krueger et al.

[11] Patent Number: 5,620,780

[45] Date of Patent: *Apr. 15, 1997

[54] COMPOSITE MATERIALS AND PROCESS

[75] Inventors: Dennis L. Krueger, Hudson, Wis.; Leigh E. Wood, Woodbury, Minn.; Michael R. Gorman, Lake Elmo, Minn.; Randall L. Alberg, Woodbury, Minn.

[73] Assignee: Minnesota Mining and Manufacturing Company, St. Paul, Minn.

[*] Notice: The term of this patent shall not extend beyond the expiration date of Pat. No. 5,429,856.

[21] Appl. No.: 427,424

[22] Filed: Apr. 24, 1995

Related U.S. Application Data

[63] Continuation of Ser. No. 225,095, Apr. 8, 1994, Pat. No. 5,429,856, which is a continuation of Ser. No. 971,277, Nov. 4, 1992, abandoned, which is a continuation-in-part of Ser. No. 502,331, Mar. 30, 1990, abandoned.

[51] Int. Cl.$^6$ .................................. D06N 7/04; C09J 7/02
[52] U.S. Cl. ........................... 428/179; 428/152; 428/354; 428/376; 604/370; 604/387; 604/389; 604/392
[58] Field of Search ....................... 428/230, 231, 428/343, 354, 373, 375, 376, 179, 152; 604/387, 370, 389, 392

[56] References Cited

U.S. PATENT DOCUMENTS

| | | | |
|---|---|---|---|
| Re. 22,038 | 2/1942 | Milas | 204/156 |
| Re. 31,922 | 6/1985 | Mesek et al. | 604/385 A |
| 2,244,422 | 6/1941 | Guba | 198/194 |
| 2,509,674 | 5/1950 | Cohen | 128/284 |
| 3,265,765 | 8/1966 | Holden et al. | 260/876 |
| 3,365,315 | 1/1968 | Beck et al. | 106/40 |
| 3,479,425 | 11/1969 | Lefevre et al. | 264/171 |
| 3,485,912 | 12/1969 | Schrenk et al. | 264/171 |
| 3,557,265 | 1/1971 | Chisholm et al. | 264/47 |
| 3,560,292 | 2/1971 | Butter | 156/229 |
| 3,562,356 | 2/1971 | Nyberg et al. | 260/876 |
| 3,616,770 | 11/1971 | Blyther et al. | 112/121.26 |
| 3,639,917 | 2/1972 | Althouse | 2/270 |
| 3,694,815 | 10/1972 | Burger | 2/224 A |
| 3,700,633 | 10/1972 | Wald et al. | 260/880 B |
| 3,800,796 | 4/1974 | Jacob | 128/284 |
| 3,860,003 | 1/1975 | Buell | 128/287 |
| 4,116,917 | 9/1978 | Eckert | 260/33.6 AQ |
| 4,152,387 | 5/1979 | Cloeren | 264/171 |
| 4,156,673 | 5/1979 | Eckert | 260/33.6 AQ |
| 4,177,812 | 12/1979 | Brown et al. | 128/284 |
| 4,197,069 | 4/1980 | Cloeren | 425/131.1 |
| 4,227,952 | 10/1980 | Sabee | 156/164 |
| 4,239,578 | 12/1980 | Gore | 156/361 |
| 4,261,782 | 4/1981 | Teed | 156/361 |
| 4,300,562 | 11/1981 | Pieniak | 128/287 |
| 4,300,967 | 11/1981 | Sigl | 156/164 |
| 4,309,236 | 1/1982 | Teed | 156/164 |
| 4,324,245 | 4/1982 | Mesek et al. | 128/287 |
| 4,352,355 | 10/1982 | Mesek et al. | 128/287 |
| 4,371,417 | 2/1983 | Prick et al. | 156/495 |
| 4,381,781 | 5/1983 | Sciaraffa et al. | 604/372 |

(List continued on next page.)

FOREIGN PATENT DOCUMENTS

| | | | |
|---|---|---|---|
| 0206349 | 12/1986 | European Pat. Off. | B29C 61/02 |
| 0320991 | 6/1989 | European Pat. Off. | A41B 13/02 |
| 2064608 | 6/1981 | United Kingdom | D06J 1/00 |
| 2160473 | 1/1987 | United Kingdom | B29C 55/00 |
| 2190406 | 4/1987 | United Kingdom | D06J 1/12 |
| WO91/07277 | 5/1991 | WIPO | B32B 5/04 |
| WO91/15364 | 10/1991 | WIPO | B32B 25/08 |
| WO92/15446 | 9/1992 | WIPO | B29C 55/02 |

*Primary Examiner*—Marion E. McCamish
*Assistant Examiner*—Blaine R. Copenheaver
*Attorney, Agent, or Firm*—Gary L. Griswold; Walter N. Kirn; William J. Bond

[57] ABSTRACT

Composite films and film laminates comprising at least one elastomeric core and a surrounding nonelastomeric matrix preferably prepared by coextrusion. The film when stretched and allowed to recover will create an elastomeric composite.

15 Claims, 7 Drawing Sheets

U.S. PATENT DOCUMENTS

| | | | |
|---|---|---|---|
| 4,386,125 | 5/1983 | Shiraki et al. | 428/36 |
| 4,389,212 | 6/1983 | Tritsch | 604/389 |
| 4,418,123 | 11/1983 | Bunnelle et al. | 428/152 |
| 4,462,819 | 7/1984 | Ales et al. | 2/400 |
| 4,476,180 | 10/1984 | Wnuk | 428/220 |
| 4,486,192 | 12/1984 | Sigl | 604/385 |
| 4,573,991 | 3/1986 | Pieniak et al. | 604/385 A |
| 4,626,305 | 12/1986 | Suzuki et al. | 156/164 |
| 4,643,729 | 2/1987 | Laplanche | 604/389 |
| 4,681,580 | 7/1987 | Reising et al. | 604/385 A |
| 4,687,477 | 8/1987 | Suzuki et al. | 604/385 A |
| 4,710,189 | 12/1987 | Lash | 604/385 A |
| 4,767,726 | 8/1988 | Marshall | 501/33 |
| 4,778,701 | 10/1988 | Pape et al. | 428/40 |
| 4,813,947 | 3/1989 | Korpman | 604/387 |
| 4,834,820 | 5/1989 | Kondo et al. | 156/73.3 |
| 4,880,682 | 11/1989 | Hazelton et al. | 428/152 |
| 4,880,706 | 11/1989 | Mazuera et al. | 428/910 |
| 4,938,753 | 7/1990 | Greenebaume, II | 222/385.2 |
| 4,940,464 | 7/1990 | Van Gompel et al. | 604/396 |
| 4,958,757 | 9/1990 | Greenebaume, II | 222/394 |
| 5,156,793 | 10/1992 | Buell et al. | 264/288.8 |
| 5,332,616 | 7/1994 | Patrick et al. | 428/910 |
| 5,344,691 | 9/1994 | Hanschen et al. | 428/152 |
| 5,354,597 | 10/1994 | Capik et al. | 428/152 |
| 5,399,219 | 3/1995 | Roessler et al. | 156/259 |
| 5,429,856 | 7/1995 | Krueger et al. | 604/370 |

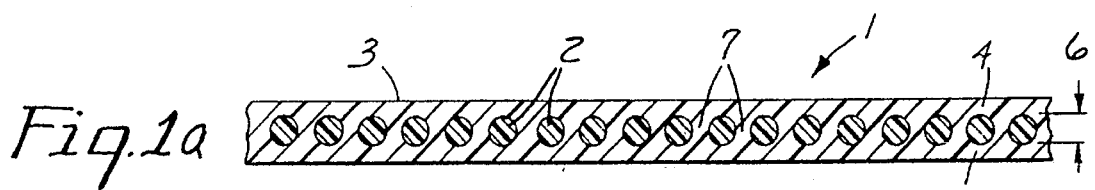
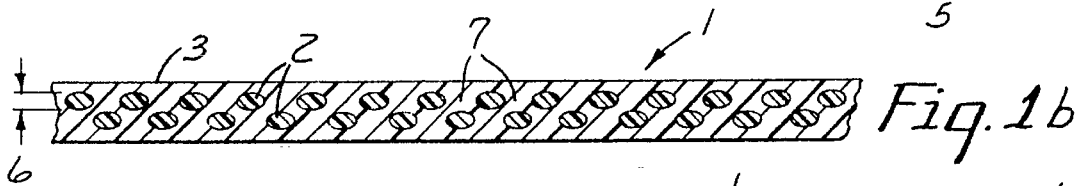
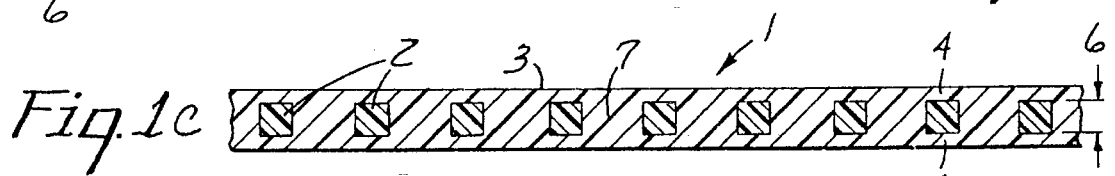
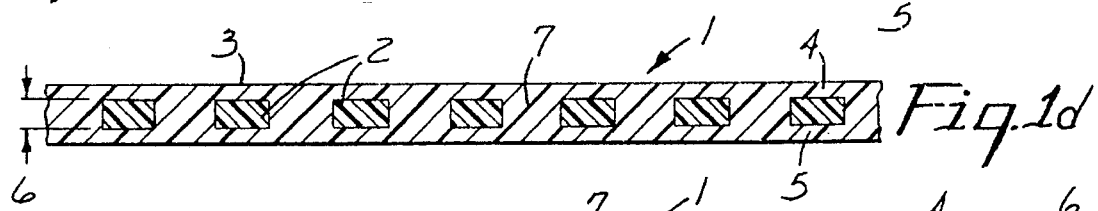
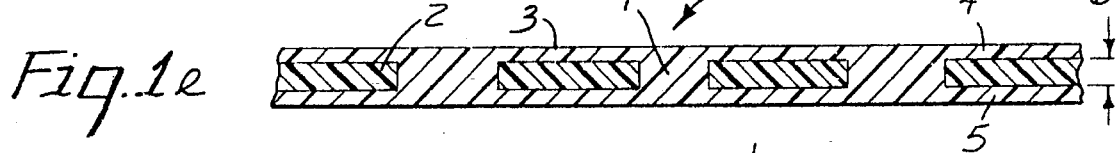
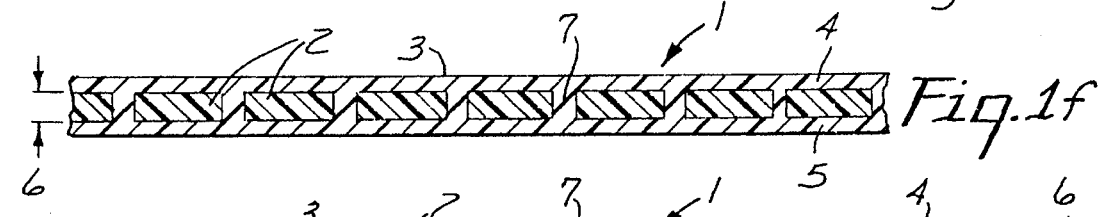
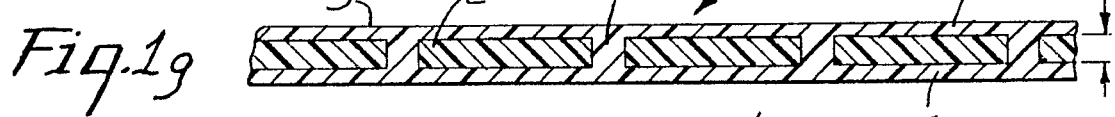
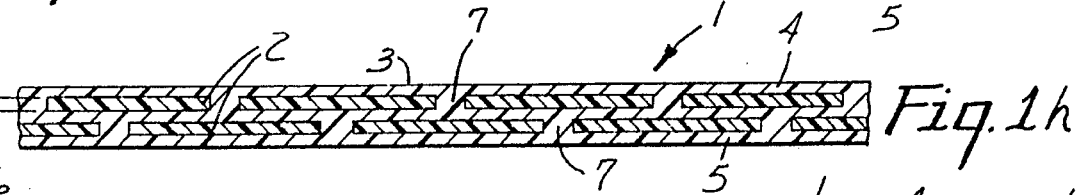
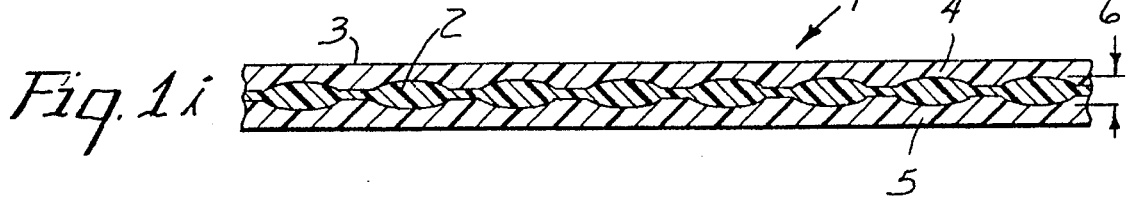

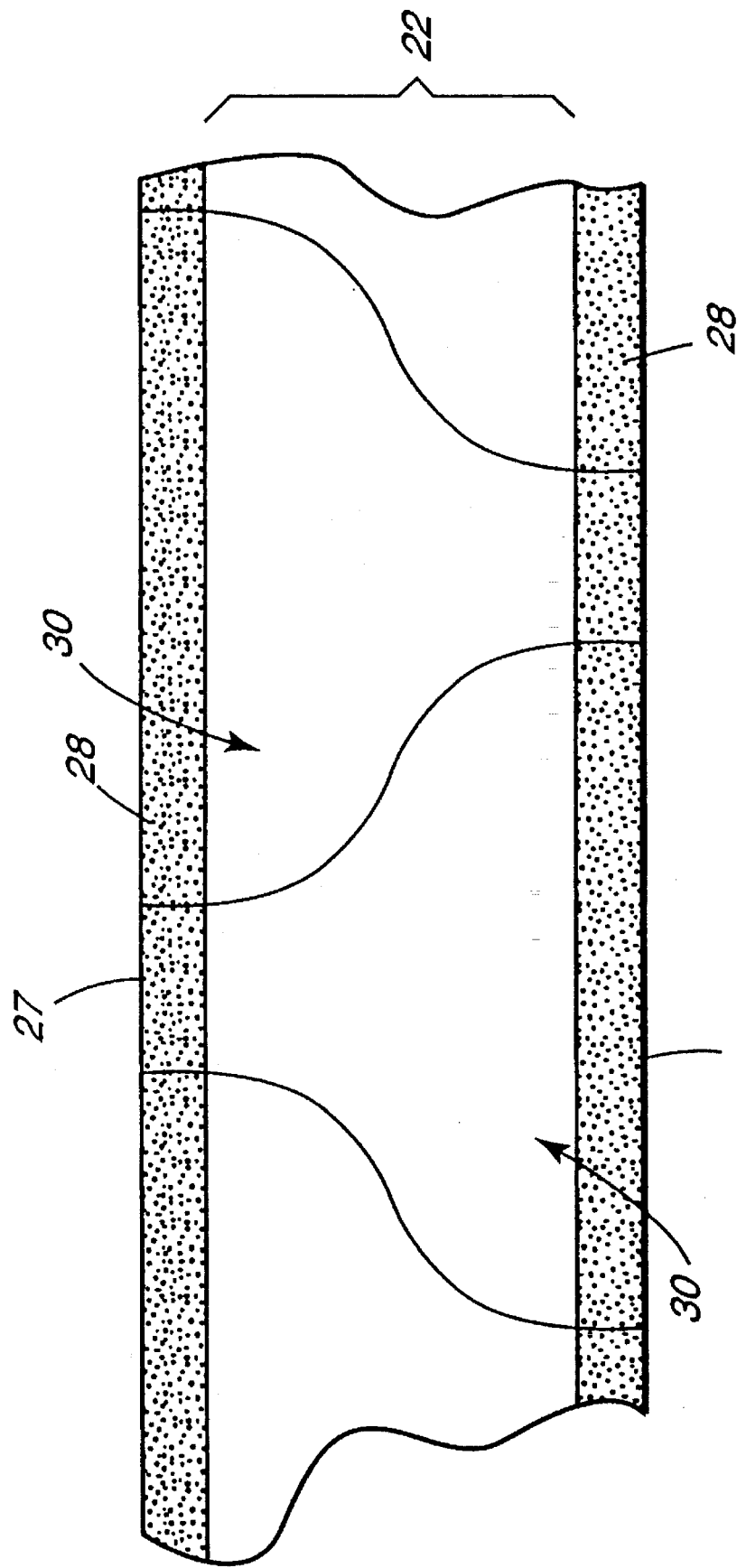

COMPOSITE MATERIALS AND PROCESS

This is a continuation-in-part application of application Ser. No. 08/225,095, filed Apr. 8, 1994, now U.S. Pat. No. 5,429,856, which is a continuation of application Ser. No. 07/971,277, filed Nov. 4, 1992, now abandoned, which is a continuation-in-part of application Ser. No. 07/502,331, filed Mar. 30, 1990, now abandoned.

Background and Field of the Invention

The invention concerns coextruded elastic composites and structures obtainable thereby.

Elastomeric materials have been long and extensively used in garments, both disposable and reusable. Conventionally, the elastic is stretched and in this stretched condition attached to a substrate. After attachment, the elastic is allowed to relax which will generally cause the substrate to shirr or gather. Elastic was at one time applied by sewing, see, e.g., U.S. Pat. Nos. 3,616,770 (Blyther et al.), 2,509,674 (Cohen), and 22,038. More recently, this procedure has been displaced by the use of adhesive, e.g., U.S. Pat. No. 3,860,003 (Buell). Buell proposed the use of an elastic strand in the leg areas of the disposable diaper. Welding has also been proposed in U.S. Pat. No. 3,560,292 (Butter) although sonic welding is preferred. A pivotal problem with all these attachment methods has been how to keep the elastic in a stretched condition while applying it to the substrate. A solution has been proposed in the use of heat shrink elastomeric materials, e.g., U.S. Pat. No. 3,639,917 (Althouse).

In diapers, for example, elastomeric bands are typically used in the waistband portions such as discussed in U.S. Pat. No. 4,681,580 (Reising et al.), and U.S. Pat. No. 4,710,189 (Lash). Both these patents describe the use of elastomeric materials which have a heat stable and a heat unstable form. The heat unstable form is created by stretching the material when heated around its crystalline or second phase transition temperature followed by a rapid quenching to freeze in the heat unstable extended form. The heat unstable elastomeric film can then be applied to the, e.g., diaper and then heated to its heat stable elastomeric form. This will then result in a desirable shirring or gathering of the waistband of the diaper. A problem with these materials, other than cost, is the fact that the temperature at which the material must be heated to release the heat unstable form is an inherent and essentially unalterable property of the material to be used. This inflexibility can cause problems. First, it is more difficult to engineer the other materials with which the waistband is associated so that they are compatible with the temperature to which the elastomeric member must be heated in order to release the heat unstable form. Frequently this temperature is rather high which can potentially cause significant problems with the adhesive used to attach the elastomeric waistband, or, e.g., the protective back sheet or top sheet of the diaper. Further, once chosen the elastomer choice can constrain the manufacturing process rendering it inflexible to lot variations, market availability and costs of raw materials (particularly elastomer(s)), customer demands, etc.

A problem noted with the application of elastic to a diaper, as proposed in U.S. Pat. No. 3,860,003, resides in the proposed use of a single relatively large denier elastomeric ribbon. This ribbon will concentrate the elastomeric force in a relatively narrow line. This allegedly caused the elastic to pinch and irritate the baby's skin. Proposed solutions to this problem included the use of wider bands of elastic as per U.S. Pat. Nos. 4,352,355 (Mesek et al.) and 4,324,245 (Mesek et al.). Allegedly, this allows the contractive forces to be distributed over a wider area and prevents irritation of the baby's skin. The preferred elastomer proposed in these applications are films of A-B-A block copolymers with a thickness of 0.5 to 5 mils. Problems noted with these films are that they are difficult to handle and must be applied with relatively complicated stretch applicators as per U.S. Pat. Nos. 4,239,578 (Gore), 4,309,236 (Teed), 4,261,782 (Teed), and 4,371,417 (Frick et al.).

An alternative solution to the pinching problem of U.S. Pat. No. 3,860,003 is proposed in the use of multiple strands of relatively small denier elastic, as per U.S. Pat. No. 4,626,305 (Suzuki et al), who describes the use of three to 45 fine rubber strings to elasticize a diaper. However, to keep the bands properly aligned they are preferably fused together. The alleged advantage in this method is that a small number of narrow elastic bands can be stretched at a high ratio to give the same tensile stress that a single equivalent diameter elastic band would yield at a lower stretch ratio. Accordingly, the stress can be distributed over a wider area and less elastic needs to be used (i.e., as the elastic is stretched more when applied). A similar approach is proposed by U.S. Pat. No. 4,642,819 (Ales et al.). However, Ales et al. uses larger denier elastic bands which act as backup elastic seals for each other when or if the diaper is distorted during use. A variation of this approach is proposed in U.S. Pat. No. 4,300,562 (Pieniak). Pieniak uses a series of interconnected elastomeric strands, in a reticulate form. Wider strands are positioned to engage the narrow portion of a tapered surface. This allegedly results in a more even distribution of stress over where the reticulate elastic engages the tapered surface. Although the use of multiple strands of elastic materials has advantages, they are more difficult to incorporate into a garment in a spaced coordinated fashion. Thin elastic strands have a tendency to wander and further present a thin profile making adhesion to the garment substrate difficult.

Spaced elastic elements are provided other than by multiple elastic strands. For example, it has been proposed to provide regionalized elastic in the waistband portion of a disposable diaper in U.S. Pat. No. 4,381,781 (Sciaraffin).

Regionalized elastic is also placed in diaper adhesive fastening tabs as per U.S. Pat. Nos. 4,389,212 (Tritsch), 3,800,796 (Jacob), 4,643,729 (Laplanche), 4,778,701 (Pape) and 4,834,820 (Kondo et al.). These patents are directed to different composite structures designed to yield a fastening tab with an elasticized central portion and inelastic or relatively rigid end portions for attachment to either side of a garment closure. These composites are quite complicated and generally are formed by adhering several separate elements together to provide the elasticized central region.

Elastomers used in these structures also exhibit relatively inflexible stress/strain characteristics which cannot be chosen independently of the activation temperature. Materials with a high modulus of elasticity are uncomfortable for the wearer. Problems with a relatively stiff or high modulus of elasticity material can be exaggerated by the coefficient of friction and necking of the elastomer which can cause the material to bite or grab the wearer.

In copending application Serial No. 07/438,593, filed Nov. 17, 1989, now U.S. Pat. No. 5,501,679 having a common assignee, there is disclosed a multi-layer elastic laminate having at least one elastomeric layer and at least one coextensive skin layer which addresses certain of the above noted problems in the art. In addition, the laminate has extremely useful and novel properties. When cast, or after formation, the elastic laminate is substantially inelastic. Elasticity can be imparted to the inelastic form of the laminate by stretching the laminate, by at least a minimum activation stretch ratio, wherein an elastic laminate material will form immediately, over time or upon the application of heat. The method by which the elastic laminate material is formed can be controlled by a variety of means. After the laminate has been converted to an elastomeric material, there is formed a novel texture in the skin layer(s) that provides significant advantages to the laminate. Despite the numerous advantages in the materials of the copending application, there is room for improvement for some applications such as those discussed above. For example, where intermittent elasticized regions are desired such as in a diaper fastening tab or where it is desirable to have discrete adjacent longitudinal bands of elastic. In these applications, laminated plastic films are less desirable. For example, they must be assembled into complex composite structures as discussed above to provide regionalized elastic. Therefore, it is desirable to retain the advantages of the material disclosed in the copending application while providing structures having regionalized elastic areas or elastic bands which can be simply constructed and are also more resistant to delamination than multi-layer laminate structures.

Summary of the Invention

The present invention relates to improved non-tacky, nonelastic material capable of becoming elastomeric when stretched. The material of the present invention is comprised both of an elastomeric polymeric core region, which provides the elastomeric properties to the material and a polymeric matrix, which is capable of becoming microtextured at specified areas. The microtextured areas will correspond to sections of the material that have been activated from an inelastic to an elastomeric form. In preferred embodiments of the present invention, the matrix material further can function to permit controlled recovery of the stretched elastomer, modify the modulus of elasticity of the elastomeric material and/or stabilize the shape of the elastomeric material (e.g., by controlling further necking). The material is preferably prepared by coextrusion of the selected matrix and elastomeric polymers. The novel, non-tacky microtextured form of the material is obtained by stretching the material past the elastic limit of the matrix polymer in predetermined elastic containing regions. The laminate then recovers in these predetermined regions, which can be instantaneous, over an extended time period, which is matrix material controllable, or by the application of heat, which is also matrix material controllable.

In certain constructions, complex periodic macrostructures can form between selectively elasticized regions depending on the method and direction of stretch activation. This can result in elastics with a considerable degree of bulk formed with relatively small amounts of elastic. This is desirable for many applications, particularly in garments.

Brief Description of the Drawings

FIG. 1 (a)–(i) are cross-sectional segments of extruded laminates of the invention before microstructuring.

FIG. 9 is a cutaway top view of a tape tab cut from a roll of the invention film material.

Figure 2A:
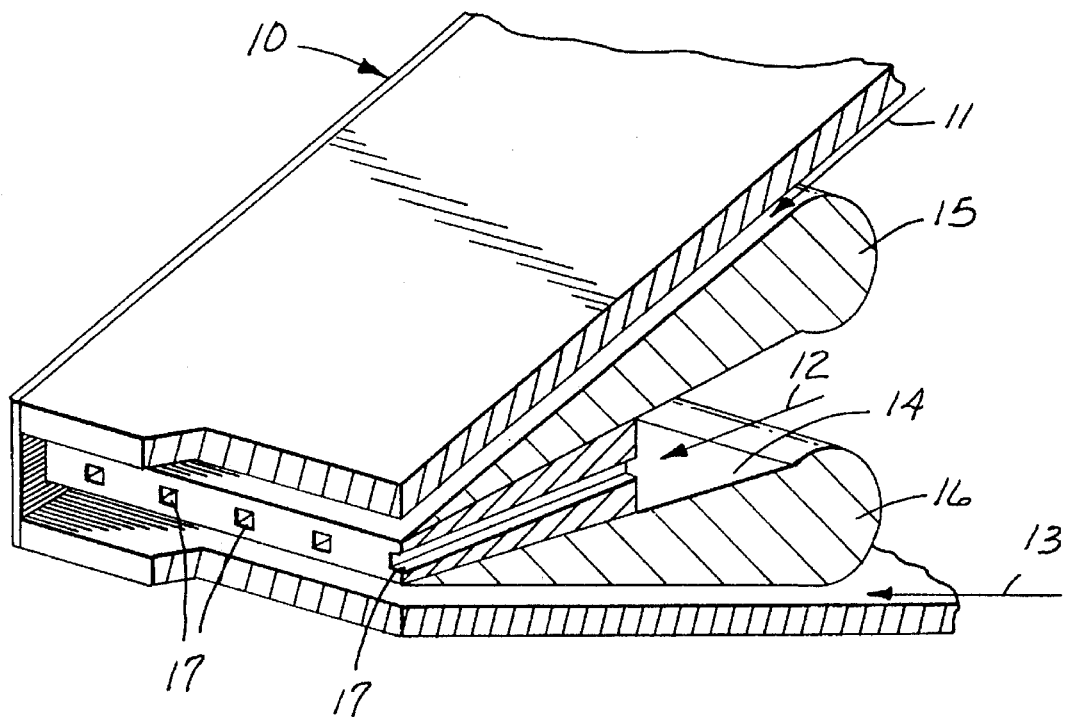
FIG. 2 is a schematic representation of a modified combining adapter used to form the invention material.

Detailed Description of Preferred Embodiments of the Invention

The present invention relates broadly to novel non-tacky nonelastic materials capable of becoming elastic when stretched comprising at least one elastomeric core region surrounded by a relatively nonelastomeric matrix. Selected regions containing the elastomeric core regions are stretched beyond the elastic limit of the surrounding matrix material. The deformed matrix is then relaxed with the core forming an elastic region having a microstructured matrix skin layer. Microstructure means that the matrix skin layer contains peak and valley irregularities or folds which are large enough to be perceived by the unaided human eye as causing increased opacity over the opacity of the laminate before microstructuring, and which irregularities are small enough to be perceived as smooth or soft to human skin. Magnification of the irregularities is usually required to see the details of the microstructured texture.

Typical constructions of the invention film material 1 are shown in FIG. 1 (a)–(i) where 2 designates the elastomeric core and 3 the matrix material. FIG. 1 is an edge view of the material as it is formed, preferably by a coextrusion process. The material is preferably in a film form. Matrix skin layers 4 and 5 in conjunction with the thickness of the core material 6 determines the performance of the material, e.g., the shrink mechanism, the microstructure, etc. The nonelastomer containing matrix region or field 7 will not recover when stretched except by gathering into periodic folds between parallel recovering elastic core containing regions.

The elastomer can broadly include any material which is capable of being formed into thin films and exhibits elastomeric properties at ambient conditions. Elastomeric means that the material will substantially resume its original shape after being stretched. Further, preferably, the elastomer will sustain only small permanent set following deformation and relaxation which set is preferably less than 20 percent and more preferably less than 10 percent of the original length at moderate elongation, e.g., about 400–500%. Generally, any elastomer is acceptable which is capable of being stretched to a degree that will cause permanent deformation in a relatively inelastic skin layer of the matrix material over the elastomer. This can be as low as 50% elongation. Preferably, however, the elastomer is capable of undergoing up to 300 to 1200% elongation at room temperature, and most preferably up to 600 to 800% elongation at room temperature. The elastomer can be both pure elastomers and blends with an elastomeric phase or content that will still exhibit substantial elastomeric properties at room temperature.

As discussed above, heat-shrinkable elastics have received considerable attention due to the ability to fabricate a product using the unstable stretched elastomer at ambient conditions and then later applying heat to shirr the product. Although these elastomers are contemplated for use in the present invention, other non-heat-shrinkable elastomers can be used while retaining the advantages of heat shrinkability with the added dimension of the possibility of substantially controlling the heat shrink process. Non-heat-shrinkable means that the elastomer, when stretched, will substantially recover sustaining only a small permanent set as discussed above. Therefore, the elastomeric core(s) can be formed from non-heat-shrinkable polymers such as block copolymers which are elastomeric such as those known to those skilled in the art as A-B or A-B-A block copolymers. These block copolymers are described, for example, in U.S. Pat. Nos. 3,265,765; 3,562,356; 3,700,633; 4,116,917 and 4,156,673, the substance of which are incorporated herein by reference. Styrene/isoprene, butadiene or ethylene-butylene/styrene (SIS, SBS or SEBS) block copolymers are particularly useful. Other useful elastomeric compositions can include elastomeric polyurethanes, ethylene copolymers such as ethylene vinyl acetates, ethylene/propylene copolymer elastomers or ethylene/propylene/diene terpolymer elastomers. Blends of these elastomers with each other or with modifying non-elastomers are also contemplated. For example, up to 50 weight percent, but preferably less than 30 weight percent, of polymers can be added as stiffening aids, such as polyvinylstyrenes, polystyrenes such as poly(alpha-methyl)styrene, polyesters, epoxies, polyolefins, e.g., polyethylene or certain ethylene/vinyl acetates, preferably those of higher molecular weight, or coumaroneindene resin. The ability to use these types of elastomers and blends provides the invention film material with significant flexibility.

Viscosity reducing polymers and plasticizers can also be blended with the elastomers such as low molecular weight polyethylene and polypropylene polymers and copolymers, or tackifying resins such as Wingtack™, aliphatic hydrocarbon tackifiers available from Goodyear Chemical Company. Tackifiers can also be used to increase the adhesiveness of an elastomeric core(s) to the matrix material. Examples of tackifiers include aliphatic or aromatic liquid tackifiers, aliphatic hydrocarbon resins, polyterpene resin tackifiers, and hydrogenated tackifying resins. Aliphatic hydrocarbon resins are preferred. Additives such as dyes, pigments, antioxidants, antistatic agents, bonding aids, antiblocking agents, slip agents, heat stabilizers, photostabilizers, foaming agents, glass bubbles, starch and metal salts for degradability or microfibers can also be used in the elastomeric core layer(s). Suitable antistatic aids include ethoxylated amines or quaternary amines such as those described, for example, in U.S. Pat. No. 4,386,125 (Shiraki), who also describes suitable antiblocking agents, slip agents and lubricants. Softening agents, tackifiers or lubricants are described, for example, in U.S. Pat. No. 4,813,947 (Korpman) and include coumarone-indene resins, terpene resins, hydrocarbon resins and the like. These agents can also function as viscosity reducing aids. Conventional heat stabilizers include organic phosphates, trihydroxy butyrophenone or zinc salts of alkyl dithiocarbonate. Suitable antioxidants include hindered phenolic compounds and amines possibly with thiodipropionic acid or aromatic phosphates or tertiary butyl cresol, see also U.S. Pat. No. 4,476,180 (Wnuk) for suitable additives and percentages.

Short fibers or microfibers can be used to reinforce the elastomeric core(s) for certain applications. These fibers are well known and include polymeric fibers, mineral wool, glass fibers, carbon fibers, silicate fibers and the like. Further, certain particles can be used, including carbon and pigments.

Glass bubbles or foaming agents are used to lower the density of the elastomeric layer and can be used to reduce cost by decreasing the elastomer content. These agents can also be used to increase the bulk of the elastomer. Suitable glass bubbles are described in U.S. Pat. Nos. 4,767,726 and 3,365,315. Foaming agents used to generate bubbles in the elastomer include azodicarbonamides. Fillers can also be used to some extent to reduce costs. Fillers, which can also function as antiblocking agents, include titanium dioxide and calcium carbonate.

The matrix can be formed of any semi-crystalline or amorphous polymer that is less elastic than the core(s) and will undergo permanent deformation at the stretch percentage that the elastomeric core(s) will undergo. Therefore, slightly elastic compounds, such as some olefinic elastomers, e.g., ethylene-propylene elastomers or ethylene-propylene-diene terpolymer elastomers or ethylenic copolymers, e.g., ethylene vinyl acetate, can be used as matrix materials, either alone or in blends. However, the matrix is generally a polyolefin such as polyethylene, polypropylene, polybutylene or a polyethylene-polypropylene copolymer, but may also be wholly or partly polyamide such as nylon, polyester such as polyethylene terephthalate, polyvinylidene fluoride, polyacrylate such as poly(methyl methacrylate)(only in blends) and the like, and blends thereof. The matrix material can be influenced by the type of elastomer selected. If the elastomeric core is in direct contact with the matrix the matrix should have sufficient adhesion to the elastomeric core(s) such that it will not readily delaminate. Where a high modulus elastomeric core(s) is used with a softer polymer matrix, a microtextured surface may not form.

Additives useful in the matrix include, but are not limited to, mineral oil extenders, antistatic agents, pigments, dyes, antiblocking agents, provided in amounts less than about 15%, starch and metal salts for degradability and stabilizers such as those described for the elastomeric core(s).

Other layers may be added between the core(s) and the matrix such as tie layers to improve bonding, if needed. Tie layers can be formed of, or compounded with, typical compounds for this use including maleic anhydride modified elastomers, ethyl vinyl acetates and olefins, polyacrylic imides, butyl acrylates, peroxides such as peroxypolymers, e.g., peroxyolefins, silanes, e.g., epoxysilanes, reactive polystyrenes, chlorinated polyethylene, acrylic acid modified polyolefins and ethyl vinyl acetates with acetate and anhydride functional groups and the like, which can also be used in blends or as compatiblizers in one or more of the matrix or core(s). Tie layers are sometimes useful when the bonding force between the matrix and core is low, although the intimate contact between skin and matrix should counteract any tendency to delaminate. This is often the case with a polyethylene matrix as its low surface tension resists adhesion.

One unique feature of the invention is the ability to control the shrink recovery mechanism of the film depending on the conditions of film formation, the nature of the elastomeric core(s), the nature of the skin(s), the manner and direction in which the film is stretched and the relative thicknesses of the elastomeric core and the matrix skin layer(s) over the core(s). By controlling these variables, in accordance with the teaching of this invention, the film material can be designed to instantaneously recover, recover over time or recover upon heat activation.

A film material capable of instantaneous shrink recovery is one in which the stretched elastomeric material will recover more than 15% (of the total recovery available) in 1 sec. A film capable of time shrink is one where the 15% recovery point takes place more than 1 sec., preferably more than 5 sec., most preferably more than 20 sec. after stretch, and a film capable of heat shrink is where less than 15% shrink recovery occurs to the laminate in the first 20 seconds after stretch. Percent recovery of the elastomeric core containing region is the percent that the amount of shrinkage is of the stretched length minus the original length of the elastomeric core containing region. For heat shrink materials, there will be an activation temperature which will initiate significant heat activated recovery. The activation temperature used for heat shrink recovery will generally be the temperature that will yield 50% of the total possible recovery ($T_{a\text{-}50}$) and preferably this temperature is defined as the temperature which will yield 90% ($T_{a\text{-}90}$) of the total possible recovery. Total possible recovery includes the amount of preactivation shrinkage.

Generally, where the matrix skin layers 4 and 5 over the core(s) in the preferential activation region are on average relatively thin, the film material will tend to contract or recover immediately after stretched. When the matrix skin thickness 4 and 5 is increased sufficiently, the film material can become heat shrinkable in the activated regions. This phenomenon can occur even when the elastomeric core(s) is formed from a non-heat shrinkable material. By careful selection of the thicknesses of the elastomeric core 4 and the matrix skin layer(s) 4 and 5, the temperature at which the material recovers by a set amount can be controlled within a set range. This is termed skin controlled recovery, where generally by altering the thickness or composition of the matrix skins 4 and 5 (assuming a constant matrix width in the noncore containing region for longitudinal activation), one can raise the elastic recovery activation temperature of an elastomeric core 4 by a significant degree, generally more than at least 10° F. (5.6° C.) and preferably by 15° F. (8.3° C.) and more. Although any matrix skin thickness which is effective can be employed, too thick a matrix skin 4 and 5 will cause the material to remain permanently set when stretched. Generally where an average single matrix skin is less than 30% of the film in this region, this will not occur although more complex retraction can be expected where the elastomeric core aspect ratio is small (e.g., a round core as per FIG. 1(a)). For most heat or time shrink materials, the stretched and activated regions of the film material must be cooled so that the energy released during stretching does not cause immediate heat activated elastic recovery. Fine tuning of the shrink recovery mechanism can be accomplished by adjusting the degree to which the activated regions are stretched. The more stretch, the more the film will tend to instantaneously recover.

This overall control over the shrink recovery mechanism of the activated regions of the elastic or elastomeric film material discussed above coupled with the ability to control the amount of stretch needed to activate elastic regions of the film material are extremely important advantages.

This control permits adjustment of the activation and recovery mechanism of the elastomeric film to fit the requirements of a manufacturing process thereby avoiding the need to adjust a manufacturing process to fit the shrink recovery mechanism of a particular elastomer.

One is also able to use skin controlled recovery to control the slow or time shrink recovery mechanism, as with the heat shrink mechanism. This shrink recovery mechanism occurs as an intermediate between instant and heat shrink recovery. Skin layer and stretch ratio control is possible as in the heat shrink mechanism, with the added ability to change the shrink mechanism in either direction, i.e., toward a heat or an instant shrink elastic film material.

A time shrink recovery film material will also exhibit some heat shrink characteristics and vice versa. For example, a time shrink film can be prematurely recovered by exposure to heat, e.g., at a time prior to 20 seconds after stretch.

Recovery can also be initiated for most time shrink and some low activation temperature heat shrink recovery film materials by mechanical deformation or activation. In this case, the film is scored, folded, wrinkled, or the like in the core containing regions to cause localized stress fractures that cause localized premature folding of the skin, accelerating formation of the recovered microtextured film. Mechanical activation can be performed by any suitable method such as by using a textured roll, a scoring wheel, mechanical deformation or the like.

Additives to the core discussed above can significantly affect the shrink recovery mechanism. For example, stiffening aids such as polystyrene can shift an otherwise heat shrinkable material into a time or instant shrink material. However, the addition of polypropylene or linear low density polyethylene (less than 15%) to a styrene/isoprene/styrene block copolymer core resulted in exactly the opposite effect, namely transforming time or instant shrink materials to heat shrink or no shrink materials. However, the possibility of polyolefin use in the elastomeric core is significant from a processing standpoint in permitting limited recycling of off batches and polyolefin additives can lower extruder torque.

A further unique feature of the present invention lies in the ability to significantly reduce the coefficient of friction (C.O.F.) of the activated regions of the elastic film material. The microtexturing is the major factor contributing to this C.O.F. reduction which, as discussed above, is controllable not only by the manner in which the film is stretched but also by the degree of stretch, the overall film thickness, the core and matrix compositions and the core to skin ratio. C.O.F. and the core/skin ratio are related such that as the ratio increases the C.O.F. decreases. Thus, fine texture yields lower C.O.F. values. Preferably, the C.O.F. will be reduced by a factor of 0.5 and most preferably by at least a factor of 0.1 of the microtextured film to itself, in the direction of stretch, when a microstructured surface is formed in accordance with the invention, as compared to the as cast film. This ability to reduce C.O.F. contributes to a softer texture and feel for the film, which is desirable for use in the medical and apparel fields.

Writability of the film in the activated region is also increased by the microstructured surface that results when the stretched film recovers. Either organic solvent or water-based inks will tend to flow into the microstructured surface channels and dry there. The more viscous the ink the less it will tend to wick in the microchannels of the surface and hence bleed. Similarly, the more the surface attraction between the skin layer and the ink, the better will be the writing characteristics of the microstructured surface. The writing surface characteristics of the film can also be altered with conventional additive or surface treatment techniques to the extent that they do not interfere with microtexturing.

The overall structure of the present invention film material may be formed by any convenient matrix forming process such as by pressing materials together, coextruding or the like, but coextrusion is the presently preferred process for forming a material with elastomeric cores within a relatively nonelastomeric material matrix. Coextrusion per se is known and is described, for example, in U.S. Pat. Nos. 3,557,265 (Chisholm et al), 3,479,425 (Leferre et al.), and 3,485,912 (Schrenk et al). Tubular coextrusion or double bubble extrusion is also possible for certain applications. The core and matrix are typically coextruded through a specialized die and feedblock that will bring the diverse materials into contact while forming the material.

The composite film materials shown in FIG. 1 can be formed, for example, by the apparatus described in Schrenk et al. Schrenk et al. employs a single main orifice and polymer passageway die. In the main passageway, which would carry the matrix material, is a nested second housing having a second passageway. The second passageway would have one or more outlets, each defining an elastomeric core, which discharges matrix material flowstreams into the main passageway matrix flow region. This composite flow then exits the orifice of the main passageway.

Figure 2B:
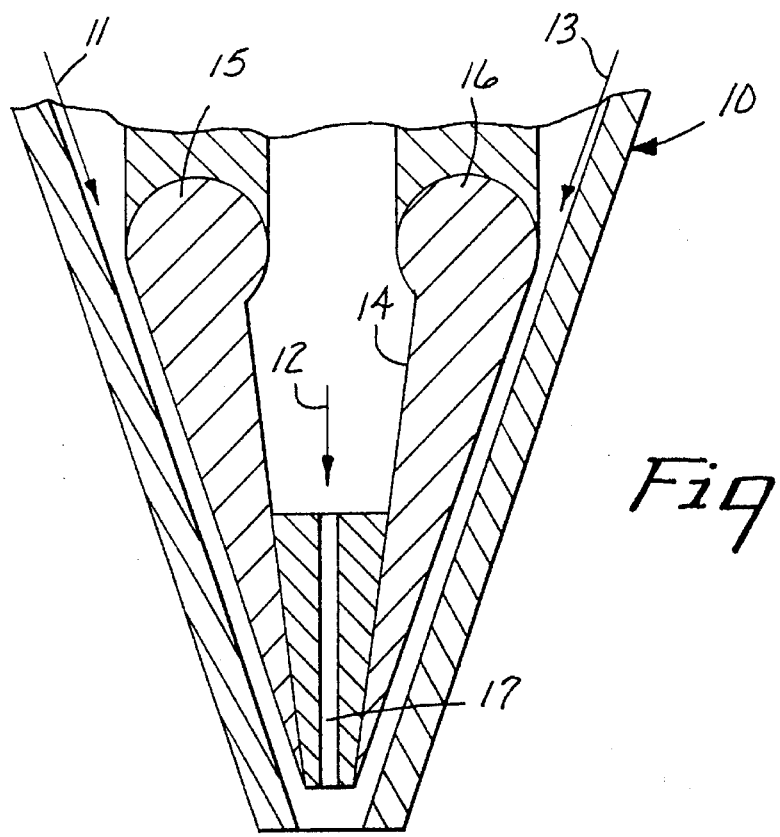
Figure 3:
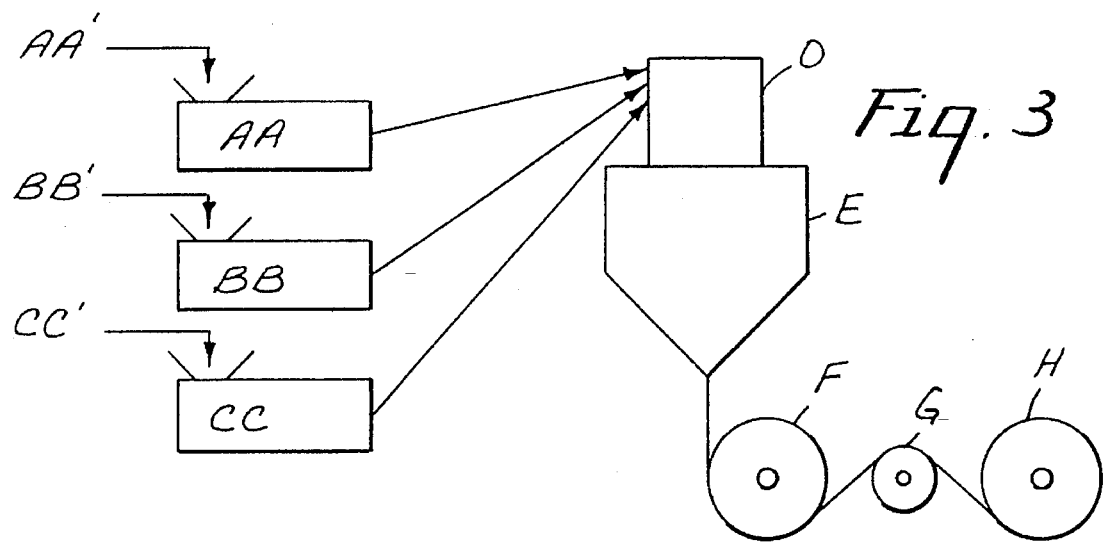
FIG. 3 is a schematic representation of a process and apparatus used to coextrude the laminates of the invention.

Another advantageous coextrusion process is possible with a modified multilayer, e.g., a three-layer, die or combining adapters such as made by Cloeren Co., Orange, Tex. Combining adapters are described in U.S. Pat. No. 4,152,387 (Cloeren) discussed above. Streams of thermoplastic materials flowing out of extruders, or from a specialized multilayer feedblock, at different viscosities are separately introduced into the die or adapter, and the several layers exiting the flow restriction channels converge into a melt laminate. A suitably modified Cloeren type adapter 10 is shown in FIG. 2 (a) and (b). Three separate polymer flow streams, 11, 12 and 13 are separated and regulated by veins 15 and 16. Streams 11 and 13 are of the matrix polymer (which in this case may be different polymers) while stream 12 is the elastomeric core polymeric material. Flow 12 is intercepted by insert 14 with cutouts 17, which can be the same or different size, which permits passage of elastomeric materials. The insert is generally attached to one vane and snuggly engaged with the second to allow the vanes to rotate in unison. This allows adjustment of the core material position within the matrix. Streams 11, 13 and the flow from stream 12 through cutouts 17 converge and form the invention film material(a five layer combining adapter is also useable to incorporate tie layers in the matrix. The combining adapter is used in conjunction with extruders, optionally in combination with multilayer feedblocks, supplying the thermoplastic materials. Such a scheme for producing the present invention film material is shown schematically in FIG. 3, for a three layer adapter, to form basic materials such as those shown in FIG. 1. AA, BB, and CC are extruders. AA', BB' and CC' are streams of thermoplastic material flowing into the feedblock or manifold die. D is the 3 or more (e.g., 5-layer) layer feedblock. E is the die and/or combining adapter, F is a heated casting roll, and G and H are rolls to facilitate take-off and roll-up of the film material.

The die and feedblock used are typically heated to facilitate polymer flow and layer adhesion. The temperature of the die depends upon the polymers employed and the subsequent treatment steps, if any. Generally the temperature of the die is not critical but temperatures are generally in the range of 350 to 550° F. (176.7 to 287.8° C.) with the polymers exemplified.

The invention film material has an unlimited range of potential widths, the width limited solely by the fabricating machinery width limitations. This allows fabrication of zone activatable microtextured elastic films for a wide variety of potential uses.

Figure 6:
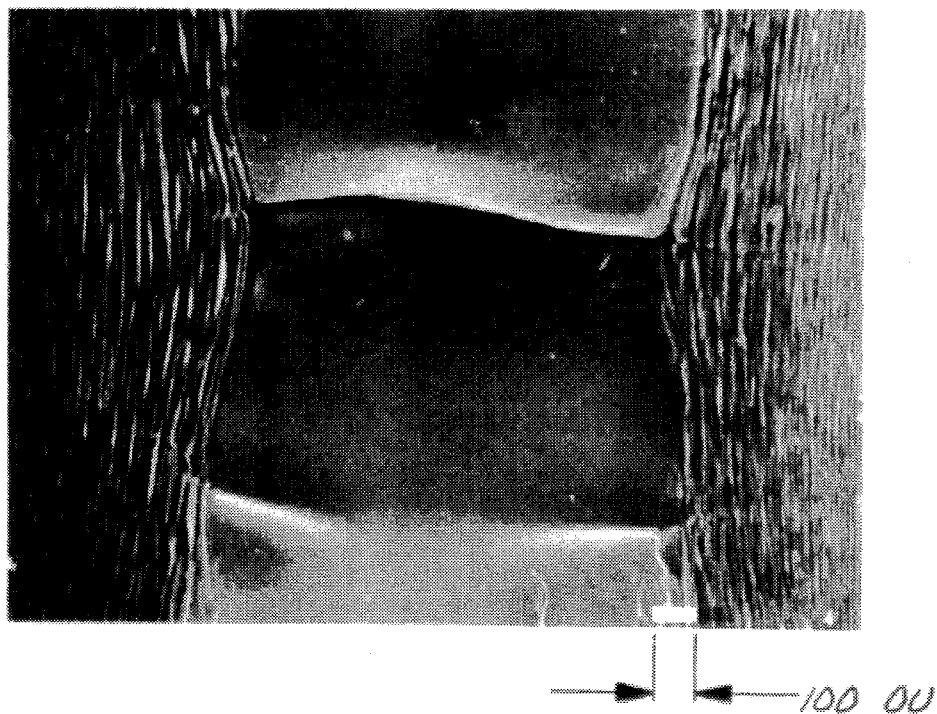
FIG. 6 is a scanning electron micrograph (100X) of a film material that has been uniaxially stretched transverse to the extruder machine direction.
Figure 7:
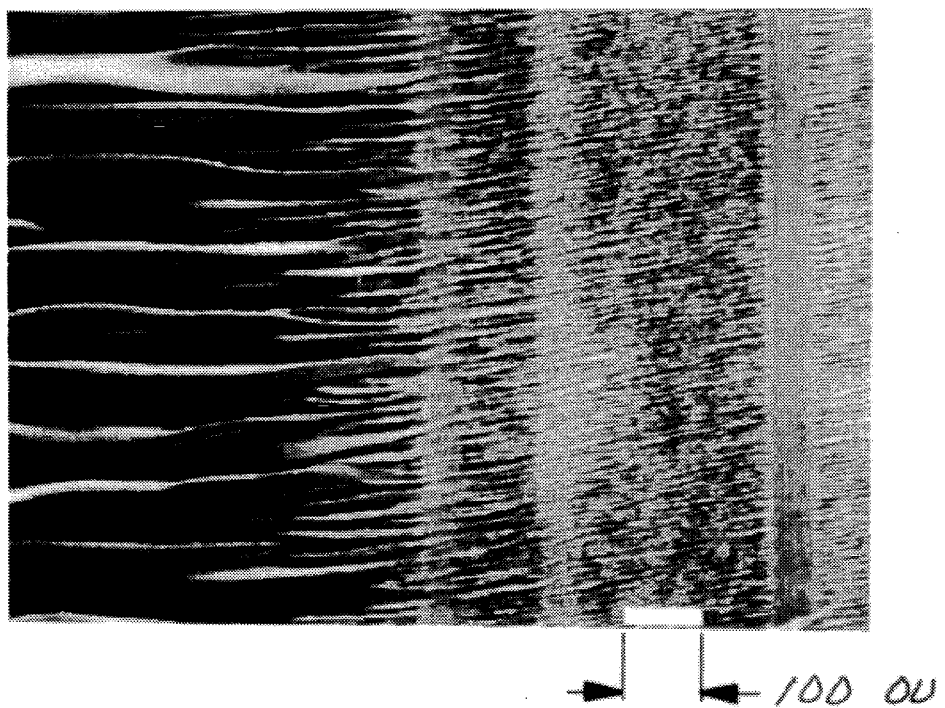
FIG. 7 is a scanning electron micrograph (100X) of the film material of FIG. 5 uniaxially stretched in the machine direction showing periodic macrostructure folding.
Figure 8:
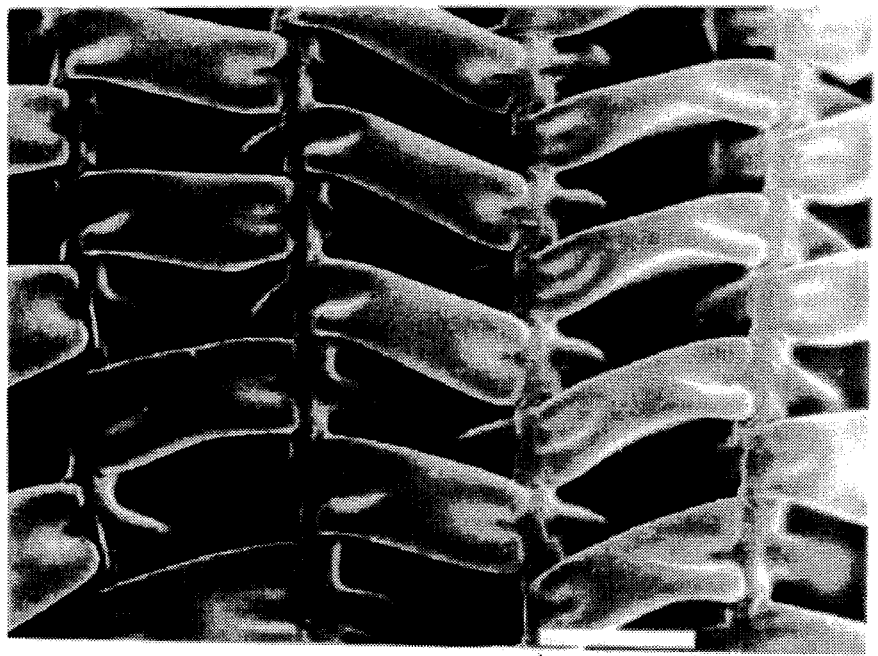
FIG. 8 is a scanning electron micrograph(1000x) of a film material uniaxially stretched in the machine direction showing periodic macrostructure folding.

The regionally elasticizable film material formed in accordance with the invention will have longitudinal bands of elastomeric material in a matrix of relatively nonelastomeric material. When this structure is stretched a microstructured surface will form in the matrix skin regions 4 and 5 of FIG. 1. This is shown in FIGS. 6 and 7 for transverse (to the machine direction) and longitudinal stretching and relaxing, respectively. Regions or fields 7 between the elastomeric cores 2, when the film is stretched longitudinally (i.e. in the machine direction), will gather into folds, as shown in FIGS. 7 and 8 for two different films. These folds will be several orders of magnitude larger than the microtexture on skin regions 4 and 5. This can add significant amounts of volume to the elastic film, a desirable quality for use in garments and for certain protective packaging. The longitudinally stretched matrix material will also contribute to the recovery mechanism of the film so stretched.

The fold structure in regions 7 will depend on the spacing between adjacent elastomeric bands 2 and the degree to which the film is stretched and recovered, as seen in FIGS. 7 and 8 above. Folds superimposed on a microstructured surface is possible with structures such as 1(b), (h) and (i) where multiple or irregular elastic cores could lead to differing levels of recovery across the film. These embodiments would yield differing microstructures across the film surface as well as folds in lower recovery areas between areas of higher recovery.

When the invention film material is stretched transversely to the elastomeric core bands (i.e., in the cross direction), the material will stretch in the regions containing the elastomeric cores 2 and possibly in nonelasticized regions 7. However, region 7 should generally yield after the elasticized regions, due to the general lower modulus of the elastomeric material 2, as per FIG. 6. However, if regions 7 have a significantly lower caliper than the elastomer containing regions, due to die swell and flow characteristics, region 7 may yield with or prior to the elastomeric core containing regions. When nonelastomer containing regions 7 stretch, they will not recover, therefore increasing the distance between the elastomeric bands, which will recover in the direction of stretch as discussed elsewhere. Activation can also be preferential in areas having higher elastomer content. For example, in FIG. 1(h) the film would tend to elongate preferentially in regions where there is an overlap in elastomeric cores or bands 2.

Figure 4:
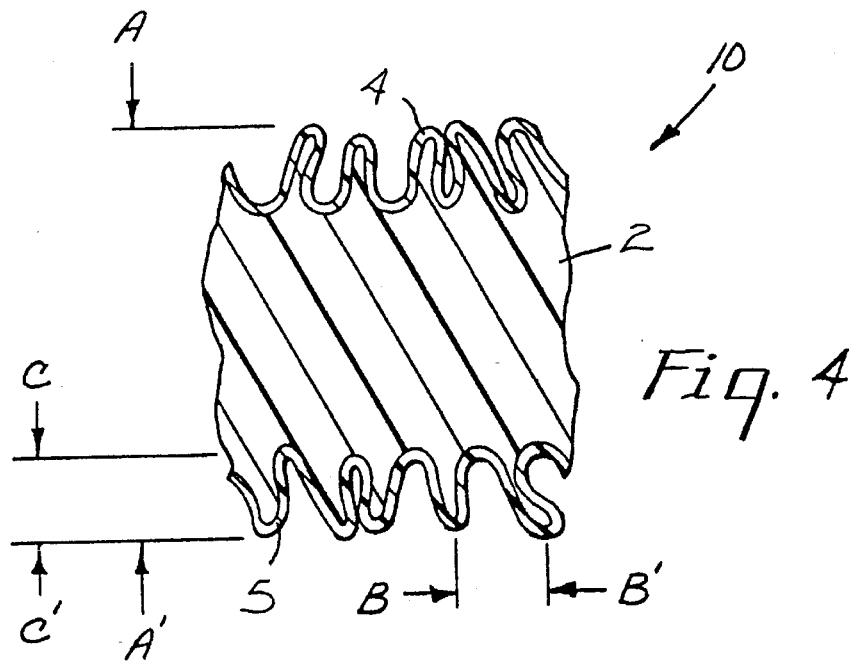
FIG. 4 is a schematic of the microstructure formed in the elastomeric regions of the invention film material that has been uniaxially stretched.

FIG. 4 is a schematic diagram of the common microstructure dimensions which are variable for uniaxially stretched and recovered films in the activated regions. The general texture is a series of regular repeating folds. These variables are the total height A–A ', the peak-to-peak distance B–B ', and the peak-to-valley distance C–C'.

Multiaxially stretching may be desirable where a more complex microstructure is desired. Biaxially, e.g., stretching creates unique surfaces while creating a film which will stretch in a multitude of directions and retain its soft feel.

It has also been found that the fold period of the microstructured surface is dependent on the core/skin ratio. This is, again, another indication of the control possible by careful choice of the parameters of the present invention.

When the film is stretched first in one direction and then in a cross direction, the folds formed on the first stretch become buckled folds and can appear worm-like in character with interspersed cross folds. Other textures are also possible to provide various folded or wrinkled variations of the basic regular fold. When the film is stretched in both directions at the same time, the texture appears as folds with length directions that are random. Using any of the above methods of stretching, the surface structure is also dependent, as stated before, upon the materials used, the thickness of the layers, the ratio of the layer thicknesses and the stretch ratio. For example, the extruded multi-layer film can be stretched uniaxially, sequentially biaxially, or simultaneously biaxially, with each method giving a unique surface texture and distinct elastomeric properties.

The degree of microtexturing of elastic laminates prepared in accordance with the invention can also be described in terms of increase in skin surface area. Where the film shows heavy textures, the surface area will increase significantly. Generally, the microtexturing will increase the surface area by at least 50%, preferably by at least 100% and most preferably by at least 250%. The increase in surface area directly contributes to the overall texture and feel of the film surface.

Increased opacity of the matrix skin also results from the microtexturing. Generally, the microtexturing will increase the opacity value of a clear film to at least 20%, preferably to at least 30%. This increase in opacity is dependent on the texturing of the skin regions with coarse textures increasing the opacity less than fine textures. The opacity increase is also reversible to the extent that when restretched, the film will clear again.

With certain constructions, the underlying elastomer may tend to degrade over time. This tendency may particularly occur with ABA block copolymers. Residual stress created during the stretching and recovery steps of activating the material to its elastomeric form can accelerate this process significantly. For those constructions prone to such degradation, a brief relaxing or annealing following activation may be desirable. The annealing would generally be above the glass transition point temperature ($T_g$) of the elastomer, above the B block $T_g$ for ABA block copolymers, but below the skin polymer melting point. A lower annealing temperature is generally sufficient. The annealing will generally be for longer than 0.1 seconds, depending on the annealing temperature. With commercial ABA block copolymers (e.g., Kraton™ 1107) an annealing or relaxing temperature of about 75° C. is found to be sufficient.

The film formed in accordance with the above description of the invention will find numerous uses due to the highly desirable properties obtainable. For example, the microtexture and macrostructures give the elastic film material a soft and silky feel as well as increased bulk. However, the softness of the elastic film, and strength in the elastic regions, can be advantageously increased by laminating a fibrous web, or other layer, to the film. This lamination is enhanced by the nonelasticized regions 7, which do not form a microstructure thereby enhancing adhesion between the elastic film and the fibrous web or the like, also forming a suitable surface for coating an adhesive or attaching a mechanical fastener element. In the elastomeric core 2 containing region(s), a fibrous web laminated to the elastic film can also limit extensibility of the elastic core 2 containing regions. Preferably, the fibrous web is a nonwoven web such as a consolidated or bonded carded web, a meltblown web, a spunbond web, a spunlace web or the like. The fibrous web is preferably bonded or laminated to the film by adhesives, thermobonding, ultrasonic welding or the like when at least the nonelastic regions 7 are substantially flat, e.g., prior to stretching or while stretching the film, for longitudinal and transverse stretching, where the elastic activated portions of the film laminate can further be non-necking. The fibrous web can also be attached after stretching and recovering the elastic film for transverse stretched webs. Alternatively, the invention film can be directly extruded onto one or two fibrous webs. The fibrous web must be extensible when attached to the film prior to stretching the film and preferably the fibrous web will not fully recover when stretched with the film such that the fibrous web will form pleats in the elastic region when the elastic region recovers.

Transverse stretched nonwoven film laminates are particularly advantageous in that they will be substantially flat and elastic in one direction and nonextensible, under typical tensioning forces used in diaper and like web assembly production lines, in the opposite direction. This makes these laminates particularly advantageous where a soft one directional elastic is needed, such as a training pant side panel. Longitudinally stretched nonwoven film laminates are less desirable in these uses in that they are not flat, have less resistance to extensibility in the nonelastic direction and can not be handled easily by longitudinally unwinding from a roll.

The elastic film or film laminate can be extensively used in disposable diapers, for example as a waistband, located in either the front or side portions of the diaper at waist level, as leg elastic or in adjustable slip-on diapers, where the elastic film could be used as, or in, side panels around the hip that have zones of elasticity to create a tight fitting garment. The films or film laminates can be applied as continuous or intermittent lengths by conventional methods. When applied, a particular advantage of the elastic film is the ability to use thin zones of elastomers with high stretch ratios while activation of the elastic film can occur at a controlled stretch ratio (particularly when stretching transverse to the elastic band longitudinal direction), depending on the size of the elastomeric core containing regions, their activation stretch ratio and modulus behavior.

When used to provide intermittent zones of elasticity the film material or a film laminate formed by, e.g., coextrusion can be cut laterally into strips containing portions of one or more elastomeric cores or bands. The elastic containing region(s) will be spaced by proper choice of the widths of nonelastic regions 7 and elastomeric core(s) 6. The elastic portion of the film or film laminate can thus be placed at the proper location to be elasticized in the finished article, see e.g., U.S. Pat. No. 4,381,781 (diaper waistbands). The elastic film or laminate could also be properly placed for diaper legbands, e.g., in a diaper "backsheet". The elastomeric cores 2 would be coextruded at locations proper for elasticizing the leg regions with liquid impermeable thermoplastic therebetween forming the diaper backsheet.

Figure 5:
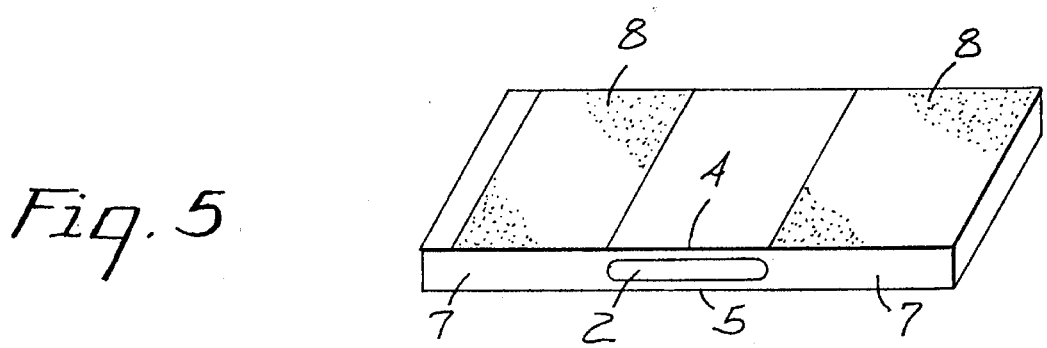
FIG. 5 is a schematic representation of a tape tab formed of the invention film material.

Another use for the invention film material, or film laminate, would be as an elasticized diaper fastening tab as per, e.g., U.S. Pat. No. 3,800,796, and shown in FIG. 5. The one or more(not shown) elastomeric core(s) 2, e.g., could be placed at the desired location while providing nonelastic end portions 7. The elasticized film is preferably 10 mm to 50 mm wide for most conventional tape tab constructions. This provides adequate tension without having to stretch the tape too far onto the diaper front. This tab could be cut from film stock containing one or more elastomeric bands 2. Adhesive 8 or a mechanical fastener (e.g., hook or loop) element could then be applied to one or more faces of the nonelastic end portions 7. However, the pressure-sensitive adhesive coated(or mechanical fastener containing, not shown) end portion 27 for releasable attaching to the diaper front portion could be 8 to 15 mm wide while the end portion 29 permanently attached to the diaper side is widened substantially, as shown in FIG. 9 and disclosed in U.S. Pat. No. 5,399,219.

In the form shown in FIG. 9 the tabs are cut from a continuous film or film laminate roll of stock material with one or more elastomeric bands 22. The two ends, 27 and 29, are inelastic and preferable both coated with a pressure-sensitive adhesive 28. The tab form shown in FIG. 9 would result in no waste (end portion 27 is an inverted mirror image of end portion 29), however, other shapes or tab designs are possible where inelastic end portion 29 may or may not be adhesive coated. In the embodiment of FIG. 9, the elastics forces are distributed to a wide area along the diaper side where end 29 is attached, which results in a more stable securement and better fit resulting from wider distribution of the elastic forces along the side portion of the diaper. Generally for the embodiment of FIG. 9 and like tab forms, the terminal portion of end 29 is at least twice as wide as the terminal portion of end 27 with a gradual tapering in the elastic region therebetween.

An additional advantage with forming fastening tabs of the invention elastic film or film laminate, is the versatility available. The tabs could be sold unstretched and easily activated by the customer, alternatively the tab could be applied stretched and activated, in both cases the tacky rubber will not be exposed. An additional advantage with a stretched and activated film tab is that the activated regions will have a surface microstructure which will tend to release adhesive tape at lower application pressures. This feature can be used to form tabs with a desirable, centrally located, mechanical low adhesion backsize region, which is desirable for fastening tabs such as those disclosed in U.S. Pat. No. 4,177,812 (Brown et al.).

Garments often are shirred to give a snug fit. This shirring can be easily obtained by applying heat shrink film materials while in an unstable stretched condition and then affecting the shirr by application of heat. The elastic film material(s) can be adhered to the garment by ultrasonic welding, heat sealing and adhesives by conventional methods. Adherence would be preferably in the matrix regions 7.

The controlled relaxation obtainable by adjusting the layer ratios, stretch ratio and direction, and layer composition makes the elastic film of the invention well suited to high speed production processes where heat activated recovery can be controlled easily by hot fluids such as hot air, microwaves, UV radiation, gamma rays, friction generated heat and infrared radiation. With microwaves, additives, such as iron whiskers, aluminum flakes or nickel powder, may be needed to ensure softening of the skin to effect skin controlled recovery.

The counter-balancing of the elastic modulus of the elastomeric core and the deformation resistance of the matrix material also modifies the stress-strain characteristics of the activated regions of the film material. The modulus therefore can be modified to provide greater wearer comfort when the film material is used in a garment. For example, a relatively constant stress-strain curve can be achieved. This relatively constant stress-strain curve can also be designed to exhibit a sharp increase in modulus at a predetermined stretch percent. The non-activated or non-stretched film as such is easier to handle and much better suited to high speed production processes than would be a conventional elastic.

The composite elastic film or film laminate is also extremely well suited for use as a tape backing providing a high loft elastic tape with excellent oxygenation resistance, tearability, self-adhesiveness and repositionability to flat surfaces. The increased tearability is advantageous in applications where each elastic strand is applied separately to a substrate such as a garment. In such garment applications, the tape can be readily torn between the elastic strand-containing regions, particularly when oriented in the longitudinal direction (i.e., parallel to the elastic strands). The elastic strands would be easily handled prior to separation and could then be applied as separate elastic strands by known methods.

The following Examples are provided to illustrate presently contemplated preferred embodiments and the best mode for practicing the invention, but are not intended to be limiting thereof.

Example 1

A continuous extrusion was carried out using a modified Cleoren$^M$ combining adapter such as shown in FIG. 2(a and b). The insert 14 was provided with seven outlets 17. The outlets width (1–7) (0.125 in (0.32 cm) high) measured, respectively, in inches 0.125 (0.318 cm), 0.313 (0.795 cm), 0.250 (0.635 cm), 0.125 (0.318 cm), 0.188 (0.478 cm), 0.375 (0.953 cm) and 0.125 (0.318 cm). The middle 5 outlets were spaced 3 inches (7.62 cm) apart while the end outlets were 2 inches (5.08 cm) from the next outlet. The veins 15 and 16 had a slight inward bevel at the rounded upstream portion that tended to create a higher volumetric flow into the central openings. In each sample, the polymeric matrix material was Fina 3576 (Fina Oil and Chemical Co., Deer Park, Tex.) polypropylene. The core material was based on an SEBS (styrene-ethylene butylene-styrene) block copolymer Kraton™ G1657 (Shell Chemical Co., Beaupre, Ohio) with varying amounts of additives listed in Table 1 below, the remaining material being elastomer.

TABLE 1

| Sample # | PAMS[1] | Pigment | Irganox[2] |
|---|---|---|---|
| A | — | 2% | — |
| B | 10% | 2% | 1% |
| C | 15% | 2% | 1% |
| D | 10% | 2% | — |

[1]Poly(alpha-methyl)styrenes, Amoco 18–210 (Amoco Oil Co., Chicago, IL)
[2]Irganox 1076 antioxidant (Ciba-Geigy Co., Hawthorne, NY)

The polypropylene was extruded from a 48 mm Rheotec™ (Rheotec Extruder, Inc., Verona, N.J.) extruder into the Cloeren™ (Cloeren Co., Orange, Tex.) die. The elastomer was extruded from a 2 inch(5.1 cm ), 4D ratio, screw diameter Berlyn™ extruder (Berlyn Corp., Worchestor, Mass.). The material was extruded onto a 45° F. (7.2° C.) chrome casting wheel without a nip roll. For sample A the Rheotec™ operated at 40 RPM with a gear pump at 28 RPM and a head PSI of 1050 (74 kg/cm$^2$). The Berlyn™ operated at 5 RPM with no gear pump and a head PSI of 1800 (127 kg/cm$^2$). The Cloeren™ operated at 360° F. (182° C.). Samples B through D operated at the same conditions except the Rheotec™ screw RPM was 28, its gear pump RPM was 40, and head pressure was 1000 PSI(70 kg/cm$^2$), and the Berlyn™ screw RPM was 4 with a head PSI of 1100 (77 kg/cm$^2$).

The samples produced and their characteristics are shown in Table 2 below.

TABLE 2

| SAMPLE | SKIN | CALIPER (mm) CORE | SKIN | AVE. CORE/SKIN RATIO | INITIAL | ELASTIC WIDTH @ NDR | FINAL | ELASTIC | OVERALL CALIPER PP | RATIO | COMMENTS |
|---|---|---|---|---|---|---|---|---|---|---|---|
| A | 0.046 mm | 0.036 mm | 0.064 mm | 0.65 | 9 mm | 9 mm | 9 mm | 0.178 mm | 0.099 mm | 1.79 | stretch in PP |
|   | 0.018 | 0.112 | 0.020 | 5.87 | 10 | 37 | 12 | 0.152 | 0.089 | 1.71 | elastic |
|   | 0.023 | 0.089 | 0.020 | 4.12 | 11 | 38 | 13 | 0.130 | 0.097 | 1.34 | elastic |
|   | 0.020 | 0.076 | 0.020 | 3.75 | 17 | 58 | 21 | 0.137 | 0.102 | 1.35 | elastic |
|   | 0.031 | 0.076 | 0.036 | 2.31 | 12 | 51 | 51 | 0.163 | 0.099 | 1.64 | stretch in PP and elastic |
| B | 0.033 mm | 0.056 mm | 0.046 mm | 1.42 | 14 mm | 14 mm | 14 mm | 0.140 mm | 0.089 mm | 1.57 | stretch in PP |
|   | 0.028 | 0.091 | 0.031 | 2.78 | 15 | 58 | 20 | 0.145 | 0.097 | 1.50 | elastic |
|   | 0.020 | 0.122 | 0.036 | 4.00 | 8 | 25 | 9 | 0.155 | 0.099 | 1.56 | elastic |
|   | 0.028 | 0.097 | 0.023 | 3.80 | 11 | 35 | 13 | 5.5 | 3.0 | 1.83 | elastic |
|   | 0.046 | 0.076 | 0.033 | 1.94 | 12 | 12 | 12 | 0.155 | 0.081 | 1.91 | stretch in PP |
| C | 0.056 mm | 0.069 mm | 0.036 mm | 1.50 | 14 mm | 56 mm | 56 mm | 0.155 mm | 0.099 mm | 1.56 | non retraction |
|   | 0.018 | 0.091 | 0.018 | 5.14 | 18 | 61 | 23 | 0.145 | 0.104 | 1.39 | elastic |
|   | 0.023 | 0.089 | 0.031 | 3.33 | 10 | 32 | 12 | 0.155 | 0.107 | 1.45 | elastic |
|   | 0.023 | 0.089 | 0.025 | 3.68 | 13 | 38 | 15 | 0.145 | 0.086 | 1.68 | elastic |
|   | 0.051 | 0.079 | 0.038 | 1.77 | 12 | 12 | 12 | 0.163 | 0.091 | 1.78 | stretch in PP |
| D | 0.046 mm | 0.076 mm | 0.051 mm | 1.56 | 13 mm | 40 mm | 40 mm | 0.160 mm | 0.099 mm | 1.62 | no retraction |
|   | 0.018 | 0.079 | 0.018 | 4.43 | 17 | 62 | 22 | 0.142 | 0.099 | 1.44 | elastic |
|   | 0.025 | 0.089 | 0.025 | 3.40 | 10 | 32 | 12 | 0.147 | 0.104 | 1.41 | elastic |
|   | 0.023 | 0.102 | 0.018 | 5.00 | 11 | 42 | 15 | 0.140 | 0.081 | 1.72 | elastic |
|   | 0.053 | 0.058 | 0.036 | 1.31 | 11 | 11 | 11 | 0.160 | 0.081 | 1.97 | stretch in PP |

The caliper of the matrix skin and core materials was measured using an optical microscope at the center of each elastic band. The elastic width was measured after casting (initial), when stretched (NDR-natural draw ratio) and when recovered (final). The overall caliper was measured using a micrometer gauge which yielded numbers generally slightly higher than the combined optical microscope readings for the matrix skin and core. The PP matrix was measured adjacent to the elastic band, usually ⅛ to ¼ inchs (0.32–0.64 cm) away. The location where the film yielded when stretched varied. Where the core to skin ratio was less than 2.5 and the overall caliper ratio was over 1.5, the film either stretched in the polypropylene matrix field of the film or would not recover when stretched in the Kraton™ core containing zones. It is believed that a higher overall caliper ratio contributes significantly to the stretching of the polypropylene matrix field. A low core/skin caliper ratio will make the material non-recoverable if stretched in the core containing region. All the samples in Table 1 were stretched in a direction perpendicular to M. D. (machine direction).

Example 2

A continuous coextrusion was carried out on the apparatus described in Example 1. The screw speed of the Rheotec™ was set at 28.0 with the gear pump at 45 RPM and the head PSI at 1000. The screw speed of the Berlyn™ was set at 4 RPM with a head PSI of 2000 (140 kg/cm$^2$). The polymer matrix was a Shell 7C50 (Shell Chemical Co., Beaupre, Ohio) polypropylene. The elastomeric core material for the four samples A–D corresponded to that of samples A–D, respectively, of Example 1. The samples were tested in a manner identical to the testing performed on samples A–D of Example 1 and the results are shown in Table 3.

TABLE 3

| SAMPLE | SKIN | CALIPER (mm) CORE | SKIN | AVE. CORE/SKIN RATIO | INITIAL | ELASTIC WIDTH @ NDR | FINAL | ELASTIC | OVERALL CALIPER PP | RATIO | COMMENTS |
|---|---|---|---|---|---|---|---|---|---|---|---|
| A | 0.056 mm | 0.041 mm | 0.036 mm | 0.89 | 10 mm | 10 mm | 10 mm | 0.168 mm | 0.089 mm | 1.89 | stretch in PP |
|   | 0.018 | 0.089 | 0.020 | 4.67 | 12 | 40 | 14 | 0.142 | 0.094 | 1.51 | elastic |
|   | 0.015 | 0.127 | 0.023 | 6.67 | 11 | 38 | 13 | 0.140 | 0.114 | 1.22 | elastic |
|   | 0.020 | 0.086 | 0.028 | 3.58 | 18 | 63 | 24 | 0.145 | 0.109 | 1.33 | elastic |
|   | 0.028 | 0.086 | 0.043 | 2.43 | 13 | 40 | 33 | 0.165 | 0.107 | 1.55 | bit retraction |
| B | 0.033 mm | 0.071 mm | 0.048 mm | 1.75 | 13 mm | 36 mm | 28 mm | 0.150 mm | 0.102 mm | 1.48 | bit retraction |
|   | 0.028 | 0.076 | 0.033 | 2.50 | 15 | 52 | 21 | 0.152 | 0.104 | 1.46 | elastic |
|   | 0.020 | 0.109 | 0.023 | 5.06 | 8 | 29 | 10 | 0.163 | 0.104 | 1.56 | elastic |
|   | 0.033 | 0.084 | 0.023 | 3.00 | 10 | 38 | 13 | 0.147 | 0.086 | 1.71 | elastic |
|   | 0.058 | 0.061 | 0.036 | 1.30 | 10 | 10 | 10 | 0.152 | 0.086 | 1.76 | stretch in PP |
| C | 0.053 mm | 0.066 mm | 0.020 mm | 1.79 | 11 mm | 11 mm | 11 mm | 0.165 mm | 0.089 mm | 1.71 | stretch in PP |
|   | 0.028 | 0.097 | 0.0234 | 3.80 | 11 | 40 | 13 | 0.158 | 0.086 | 1.71 | elastic |
|   | 0.020 | 0.114 | 0.018 | 6.00 | 9 | 30 | 10 | 0.163 | 0.109 | 1.44 | elastic |
|   | 0.018 | 0.094 | 0.023 | 4.62 | 16 | 62 | 22 | 0.152 | 0.107 | 1.40 | elastic |
|   | 0.038 | 0.076 | 0.031 | 2.22 | 13 | 40 | 27 | 0.163 | 0.102 | 1.50 | bit retraction |
| D | 0.053 mm | 0.084 mm | 0.036 mm | 1.89 | 13 mm | 43 mm | 43 mm | 0.165 mm | 0.104 mm | 1.59 | no retraction |
|   | 0.033 | 0.097 | 0.023 | 3.45 | 16 | 56 | 21 | 0.158 | 0.104 | 1.51 | elastic |
|   | 0.028 | 0.102 | 0.028 | 3.64 | 9 | 29 | 10 | 0.163 | 0.104 | 1.56 | elastic |
|   | 0.020 | 0.109 | 0.018 | 5.73 | 10 | 35 | 13 | 0.152 | 0.081 | 1.88 | elastic |
|   | 0.061 | 0.058 | 0.041 | 1.15 | 9 | 9 | 9 | 0.163 | 0.079 | 2.06 | stretch in PP |

Similar results to that seen in Example 1 were noticed.

Example 3

In this continuous coextrusion, the operating conditions of the apparatus were a variation of those of Example 1, Sample A, with the Rheotec™ screw speed increased to 45 RPM and the head PSI increased to 1050 (74 kg/cm$^2$). The RPM of the Berlyn™ was reduced to 4, and the head PSI to 1200 (84 kg/cm$^2$). The sample compositions A–D were identical to those of samples A–D of Example 1 except that Kraton™ 1107 (styrene-isoprene-styrene) was used as the elastomer.

The extrusion and stretching results for each strand are shown in Table 4 (tested as in Examples 1 and 2).

Example 4

These continuous coextrusion samples A–D had identical compositions to those of samples A–D of Example 2, Properties of the film are shown in Table 5 (tested as above), Sample E is identical to sample D except that the elastomer component contained 2% white pigment. Both heat and time shrink samples were noted. The shrink mechanisms were determined at room temperature (25° C.),

TABLE 4

| Sample | Skin | Caliper Core | (mm) Skin | Ave. Core/Skin Ratio | Initial Elastic Width | Final Elastic Width | Comments |
|---|---|---|---|---|---|---|---|
| A | 0.028 | 0.089 | 0.056 | 2.12 | 12 mm | 51 | no retraction |
|   | 0.015 | 0.079 | 0.025 | 3.88 | 17 | 19 | elastic |
|   | 0.028 | 0.103 | 0.023 | 4.00 | 9 | 11 | elastic |
|   | 0.023 | 0.107 | 0.025 | 4.42 | 12 | 13 | elastic |
|   | 0.051 | 0.081 | 0.041 | 1.78 | 11 | 11 | stretch in PP |
| B | 0.036 | 0.066 | 0.031 | 2.00 | 14 mm | 36 | no retraction |
|   | 0.018 | 0.091 | 0.023 | 4.50 | 15 | 16 | elastic |
|   | 0.020 | 0.086 | 0.025 | 3.78 | 12 | 12 | elastic |
|   | 0.023 | 0.061 | 0.028 | 2.40 | 21 | 26 | elastic |
|   | 0.036 | 0.079 | 0.041 | 2.07 | 15 | 58 | no retraction |
| C | 0.028 | 0.086 | 0.033 | 2.83 | 16 mm | 58 | no retraction |
|   | 0.015 | 0.091 | 0.018 | 5.54 | 19 | 24 | elastic |
|   | 0.025 | 0.089 | 0.023 | 3.68 | 11 | 11 | elastic |
|   | 0.020 | 0.084 | 0.031 | 3.30 | 14 | 16 | elastic |
|   | 0.038 | 0.069 | 0.025 | 2.16 | 14 | 60 | no retraction |
| D | 0.043 | 0.064 | 0.036 | 1.61 | 14 mm | 46 | heat shrink |
|   | 0.028 | 0.107 | 0.031 | 3.65 | 17 | 23 | elastic |
|   | 0.031 | 0.099 | 0.025 | 3.55 | 15 | 18 | elastic |
|   | 0.020 | 0.119 | 0.015 | 6.71 | 26 | 33 | elastic |
|   | 0.041 | 0.091 | 0.036 | 2.40 | 16 | 70 | no retraction |

As can be seen, Sample D demonstrated heat shrink characteristics at low core/skin ratios.

TABLE 5

| Sample | Skin | Caliper Core | (mm) Skin | Ave. Core/Skin Ratio | Elastic Initial | Width Final | Comments |
|---|---|---|---|---|---|---|---|
| A | 0.48 | 0.064 | 0.038 | 1.47 | 12 mm | 47 mm | no retraction |
|   | 0.043 | 0.097 | 0.031 | 2.62 | 12 | 15 | elastic |
|   | 0.028 | 0.122 | 0.025 | 4.57 | 6 | 7 | elastic |
|   | 0.031 | 0.122 | 0.025 | 4.36 | 9 | 10 | elastic |
|   | 0.031 | 0.089 | 0.058 | 2.00 | 12 | 53 | no retraction |
| B | 0.020 | 0.074 | 0.033 | 2.76 | 4 mm | 17 mm | no retraction |
|   | 0.028 | 0.091 | 0.025 | 3.43 | 15 | 39 | time shrink |
|   | 0.025 | 0.107 | 0.028 | 4.00 | 12 | 13 | elastic |
|   | 0.020 | 0.102 | 0.028 | 4.21 | 8 | 10 | elastic |
|   | 0.018 | 0.125 | 0.018 | 7.00 | 17 | 20 | elastic |
|   | 0.028 | 0.097 | 0.025 | 3.62 | 16 | 36 | time shrink |
|   | 0.023 | 0.069 | 0.025 | 2.70 | 5 | 19 | no retraction |
| C | 0.025 | 0.076 | 0.028 | 2.86 | 15 mm | 60 | slight retraction |
|   | 0.23 | 0.081 | 0.025 | 3.37 | 12 | 15 | elastic |
|   | 0.031 | 0.107 | 0.028 | 3.65 | 8 | 10 | elastic |
|   | 0.023 | 0.099 | 0.023 | 4.33 | 16 | 19 | elastic |
|   | 0.033 | 0.081 | 0.028 | 2.67 | 16 | 40 | time shrink |
| D | 0.023 | 0.086 | 0.056 | 2.19 | 6 mm | 15 mm | slight retraction |
|   | 0.031 | 0.081 | 0.031 | 2.67 | 16 | 24 | time shrink |

TABLE 5-continued

| Sample | Skin | Caliper (mm) Core | Skin | Ave. Core/Skin Ratio | Elastic Initial | Width Final | Comments |
|---|---|---|---|---|---|---|---|
|   | 0.018 | 0.137 | 0.023 | 6.75 | 17 | 21 | elastic |
|   | 0.028 | 0.107 | 0.031 | 3.65 | 9 | 10 | elastic |
|   | 0.031 | 0.099 | 0.028 | 3.39 | 13 | 14 | elastic |
|   | 0.031 | 0.086 | 0.031 | 2.83 | 16 | 25 | time shrink |
|   | 0.036 | 0.056 | 0.031 | 1.69 | 6 | 20 | bit retraction |
| E | 0.033 | 0.081 | 0.040 | 2.21 | 16 mm |   | slight retraction |
|   | 0.023 | 0.122 | 0.028 | 4.80 | 13 |   | elastic |
|   | 0.031 | 0.147 | 0.038 | 4.30 | 9 |   | elastic |
|   | 0.025 | 0.097 | 0.025 | 3.80 | 17 |   | elastic |
|   | 0.036 | 0.091 | 0.038 | 2.48 | 16 |   | time shrink |

Example 5

The insert was provided with 1/16 in. (0.158 cm) wide, 0.125 in. (0.32 cm) high holes spaced 1/16 in(0.158 cm) apart. The elastic core material was 99% Kraton™ 1107 (and 1% antioxidant fed by a 2 inch (5.08 cm) Berlyn™ extruder with zone temperatures varied from 280° F. (138° C.) to 400° F. (204° C.) at the exit, operating at 15 rotations per minute (RPM). The matrix material was a linear low density polyethylene, Dowlex™2517 (Dow Chem. Co., Rolling Meadows, Ill.) fed by a 1 in (2.54 cm) Brabender™ (C. W. Brabender Instruments, Inc., N.J.) extruder operating at 43 RPM and with zone temperatures ranging from 145° C. to 173° C., at the exit. The die and casting roll operated at 360° F. (182° C.) and 70° F. (21° C.), respectively, with the casting roll running at 11.1 and 16.8 ft (3.4 and 5.12 m/min) for samples A and B.

For sample C, the Berlyn™ extruder was run at the same conditions except the inlet zone was set at 285° F. (141° C.), and it ran at 30 RPM. The matrix material was changed to polypropylene (PP 3014) (Exxon Chem. Corp., Houston, Tex.) and run at 20 RPM in the Brabender™ (zone temperature ranging from 165° C. to 223° C.). The die and casting rolls were 400° F. and 66° F. (204° C. and 19° C.), respectively, with a roll speed of 11.5 feet (3.5 meters) per minute.

The dimensions of the material (mils and (mm)) obtained are shown in Table 6 below.

TABLE 6

| Sample # | Total Thickness at Core | Thickness Between Cores | Height Core | Space Width Core | Between Cores |
|---|---|---|---|---|---|
| A | 19 (.48) | 4 (0.01) | 17.2(0.44) | 40(1.01) | 100(2.54) |
| B | 10 (0.25) | 1.2 (0.03) | 9.2(0.23) | 24(0.61) | 92(2.34) |
| C | 5.6 (0.14) | 5.2 (0.13) | 4.8(0.12) | 114(2.90) | 116(2.95) |

The materials were all stretched 5:1 and allowed to relax instantaneously. FIG. 8 is a scanning electron micrograph of the stretched and relaxed sample B. FIGS. 6 and 7 are scanning electron micrographs of sample C, stretched uniaxially in the cross direction and machine direction, respectively. All the films show regular or periodic folding when stretched in the machine direction. In samples A and B, the thickness of the matrix material between the cores 7 appeared to be due to the low die swell of the matrix material compared to the Kraton™ elastomeric core material. In all films, the matrix material completely circumscribed the cores 7 with only the cut end of each film having exposed core material.

In sample C, the die swell of the core and matrix materials were very similar and the film formed had a relatively flat profile. The core material in sample C was also fed at a considerably higher relative rate, to the matrix in sample C, as compared to samples A and B, resulting in a considerably larger elastomeric core region.

Example 6

In this example, samples A–C were identical compositionally to sample C of Example 5. The Berlyn™ extruder was run at 10 RPM (zone temperatures ranging from 370° F. (188° C.) to 420° F. (216° C.). The matrix was extruded from a 2 in. (5.08 cm) Rheotec™ extruder (zone temperatures ranging from 350° F. (177° C.) to 400° F. (204° C.), operating at 61 RPM with a 400° F. gear pump at 50 RPM. The die was at 400° F. (204° C.) feeding onto a 50° F. (10° C.) casting roll operating at 54.1, 38.8 and 33.0 ft (16.5, 11.8 and 10.1 m) per minute for samples A–C, respectively.

Sample D was run using the Brabender™ extruder for the elastic (zone temperature range 380°–420° F. (193°–216° C.)) with the same elastic. The matrix was run on the above Rheotec™ arrangement with the gear pump at 20 RPM. The matrix was 90% PP 8771 (Exxon Chem. Corp. ) with 10% blue pigment. The casting roll was 50° F. (10° C.) and ran at 21.4 ft (12.2 m) per minute.

Sample E was run the same as D, except the gear pump ran at 40 ft (12.2 m) per minute, the Brabender™ at 32 RPM and the casting roll ran at 40 ft (12.2 m) per minute.

Sample F was run the same as E except the casting roll ran at 23.3 ft (7.1 m) per minute.

Sample G was run the same as F except the casting roll ran at 21.4 ft (6.5 m) per minute, and the matrix was 50% polybutylene (PB 8010 available from Shell Chem. Co., Beaupre, Ohio), 40% polypropylene (PP 3014 available from Exxon Chem. Co., Houston, Tex.) and 10% blue pigment.

Sample H was run the same as F except the skin was 70% PP 3014, 20% PB 8010 and 10% blue pigment.

The insert for this example had holes 0.125 in (0.32 cm) high, and 0.5 in (1.27 cm) wide with 4 in (10.16 cm) between holes.

The dimensions of the samples are set forth in Table 7 below, in mils (mm).

TABLE 7

| Sample Number | Total Thickness at Core | Thickness Between Cores | Height Core | Width Core | Space Between Cores |
| --- | --- | --- | --- | --- | --- |
| A | 3.5 (0.089) | 3.0 (0.076) | — | 1.4 (0.036) | 2.0 (0.051) |
| B | 4.3 (0.11) | 4.2 (0.11) | — | 1.5 (0.038) | 2.0 (0.051) |
| C | 5.1 (0.13) | 5.1 (0.13) | — | 1.4 (0.036) | 2.0 (0.051) |
| D | 8.0 (0.18) | 7.0 (0.18) | — | 1.1 (0.028) | 2.4 (0.061) |
| E | 4.2 (0.11) | 3.4 (0.088) | — | 1.0 (0.025) | 2.3 (0.058) |
| F | 4.3 (0.11) | 3.6 (0.091) | — | 0.9 (0.023) | 2.1 (0.053) |
| G | 3.7 (0.094) | 3.9 (0.099) | — | 1.3 (0.033) | 2.0 (0.051) |
| H | 5.5 (0.014) | 5.0 (0.127) | — | 1.0 (0.025) | 2.1 (0.053) |

These samples were all stretched 5:1 in the machine direction and relaxed instantaneously.

Examples 7 and 8

Samples B and C of Example 5 were coated with adhesive and were identified as Examples 7 and 8, respectively. Example 7 was coated with a hot-melt coatable, pressure-sensitive adhesive comprising a tackified synthetic block copolymer. Example 8 was laminated to a 37.5 mil thick acrylate adhesive (3M 9671SL). Both tapes were formed by applying the adhesive prior to stretching the backing. Tape 7 was adhered to itself and a glass plate after stretching in the machine direction. Tape 8 was also adhered to itself and a glass plate after stretching in the machine and cross directions. All the tapes were stretched uniaxially at a 5:1 draw ratio. The tapes were peel tested at 90 degree and 180 degree peel angles, after adhering with a 5 lb rolldown (1 minute dwell), at a peel rate of 90 in/min (5 second average value). The results are shown in Table 8 below in gm/in. "Flat" indicates the film prior to stretching and "Stretched" indicates the film after stretching and recovery. Tapes 7 and 8 (MD) tore in the machine direction.

TABLE 8

| Example | 7 | 8 (MD) | 8 (CD) |
| --- | --- | --- | --- |
| Adhesion to Glass | | | |
| 180° Flat | 1,690 | 336 | 540 |
| 180° Stretched | 561 | 312 | 317 |
| 90° Flat | 544 | 333 | 463 |
| 90° Stretched | 264 | 168 | 213 |
| Adhesion to Backside | | | |
| 180° Flat | 360 | 207 | 309 |
| 180° Stretched | 456 | 212 | 125 |
| 90° Flat | 286 | 208 | 266 |
| 90° Stretched | 140 | 120 | 191 |

For Examples 7 and 8(MD), the 180 degree Stretched Adhesion to Backside was higher than to the Flat Adhesion to Backside peel indicating that there was likely interpenetration of the macrostructure folds of the adhesive and the macrostructure folds of the backside.

The various modifications and alterations of this invention will be apparent to those skilled in the art without departing from the scope and spirit of this invention, and this invention should not be restricted to that set forth herein for illustrative purposes.

We claim:

1. A fastening tab comprising a closure layer and a backing of a coextruded film having two faces comprising at least one discrete elastomeric core containing region capable of elastic elongation and a matrix of thermoplastic polymeric material, which polymeric matrix material is less elastic than the elastomeric core material, said matrix material completely circumscribing said at least one discrete elastomeric core so that there is at least two nonelastic film regions comprising matrix material, wherein the thickness and the presence of the elastomeric core material varies across the film length and/or width and wherein when said coextruded film is stretched past the inelastic deformation limit of the matrix material around said at least one elastomeric core the film will be capable of recovery in the at least one elastomeric core containing region to form a microtextured skin layer, formed of the matrix material over the at least one elastomeric core, only in the elastomeric core containing region of said film, wherein at least one nonelastic film region contains the closure layer.

2. The fastening tab of claim 1 wherein the at least one elastomeric core comprises an extrudable polymer and said matrix material is a thermoplastic polymer.

3. The fastening tab of claim 1 wherein the at least one core is approximately at the same relative location to the two film faces.

4. The fastening tab of claim 1 wherein the at least one elastomeric core is at different locations in said film relative to the two film faces.

5. The fastening tab of claim 1 comprising a diaper closure tab.

6. The fastening tab of claim 5 where the closure layer comprises a pressure-sensitive adhesive layer.

7. The fastening tab of claim 6 wherein a low adhesion backsize is on at least the face opposite the backing face coated with the pressure-sensitive adhesive layer.

8. The fastening tab of claim 1 wherein the closure layer comprises a mechanical fastening element.

9. The fastening tab of claim 8 wherein the mechanical fastening element comprises a hook fastening element.

10. The fastening tab of claim 1 further comprising a fibrous web on at least one face of the backing.

11. The fastening tab of claim 1 further comprising a fibrous web on both faces of the backing.

12. The fastening tab of claim 11 wherein the fibrous web is a nonwoven web.

13. The fastening tab of claim 11 wherein the nonwoven web is extensible.

14. The fastening tab of claim 1 wherein one end is an inverted mirror image of the opposite end such that the tape tab can be continuously cut from the roll of tape without waste.

15. The fastening tab of claim 14 wherein the terminal portion of the one end is at least twice as wide as the terminal portion of the opposing end.

\* \* \* \* \*